United States Patent
Lezoualc'h et al.

(10) Patent No.: US 9,751,838 B2
(45) Date of Patent: Sep. 5, 2017

(54) TETRAHYDROQUINOLINE DERIVATIVES AND THEIR USE AS EPAC INHIBITORS

(71) Applicants: INSTITUT NATIONAL DE LA SANTE ET DE LA RECHERCHE MEDICALE (INSERM), Paris (FR); UNIVERSITE PAUL SABATIER TOULOUSE III, Toulouse (FR); UNIVERSITE PARIS-SUD, Orsay (FR); UNIVERSITE D'ORLEANS, Orleans (FR)

(72) Inventors: Frank Lezoualc'h, Toulouse (FR); Rodolphe Fischmeister, Chatenay-Malabry (FR); Malik Bisserier, Toulouse (FR); Pascal Bouyssou, Orleans (FR); Jean-Paul Blondeau, Chatenay-Malabry (FR); Delphine Courilleau, Chatenay-Malabry (FR)

(73) Assignees: Institut National de la Sante et de la Recherche Medicale (INSERM), Paris (FR); Universite Paul Sabatier Toulouse III, Toulouse (FR); Universite Paris-Sud, Orsay (FR); Universite d'Orleans, Orleans (FR)

( * ) Notice: Subject to any disclaimer, the term of this patent is extended or adjusted under 35 U.S.C. 154(b) by 0 days.

(21) Appl. No.: 14/432,768

(22) PCT Filed: Sep. 17, 2013

(86) PCT No.: PCT/EP2013/069298
§ 371 (c)(1),
(2) Date: Apr. 1, 2015

(87) PCT Pub. No.: WO2014/053315
PCT Pub. Date: Apr. 10, 2014

(65) Prior Publication Data
US 2015/0252002 A1  Sep. 10, 2015

(30) Foreign Application Priority Data
Oct. 2, 2012 (EP) .................................. 12306201

(51) Int. Cl.
*A01N 43/42*  (2006.01)
*A61K 31/47*  (2006.01)
*C07D 215/14*  (2006.01)
*C07D 215/08*  (2006.01)
*C07D 215/18*  (2006.01)

(52) U.S. Cl.
CPC ............ *C07D 215/14* (2013.01); *A61K 31/47* (2013.01); *C07D 215/08* (2013.01); *C07D 215/18* (2013.01)

(58) Field of Classification Search
CPC .... A61K 31/47; C07D 215/08; C07D 215/14; C07D 215/18
See application file for complete search history.

(56) References Cited

U.S. PATENT DOCUMENTS

2011/0060029 A1  3/2011  Iwatsubo et al.

FOREIGN PATENT DOCUMENTS

| DE | 102 36 910 A1 | 3/2004 |
|----|---------------|--------|
| WO | 2006/094703 A1 | 9/2006 |
| WO | 2006/133128 A2 | 12/2006 |
| WO | 2011/080264 A1 | 7/2011 |

OTHER PUBLICATIONS

Courilleau et al, The Journal of Biological Chemistry vol. 287, No. 53, pp. 44192-44202, Dec. 28, 2012.*
Freshney (Culture of Animal Cells, A Manual of Basic Technique, Alan R. Liss, Inc., 1983, New York, p. 4).*
Dermer (Bio/Technology, 1994, 12:320).*
Parnell et al, Trends in Pharmacological Sciences Apr. 2015, vol. 36, No. 4.*
Bos et al, Review, Trends in Biochemical Sciences vol. 31, No. 12, Nov. 2, 2006.*
Chen et al, J. Med. Chem., 2014, 57 (9), pp. 3651-3665.*
Almahariq et al, Trends Endocrinol Metab. Feb. 2014; 25(2): 60-71.*
Bisserier et al, Biochemical Society Transactions Apr. 1, 2014, 42 (2) 257-264.*
Brown et al, The Journal of Biological Chemistry vol. 289, No. 12, pp. 8217-8230, Mar. 21, 2014.*
Bouyssou et al., "Synthesis of 7-and 5,7-substituted-6-fluor-2-methyl-1,2,3,4-tetrahydroquinolines: Convenient precursors of quinoline antibacterial agents", Journal of Heterocyclic Chemistry, Jul. 1, 1992, pp. 895-898, vol. 29, No. 4.
Morita et al., "An Efficient Synthesis of a Key Intermediate towards(S)-(−)-Nadifloxacin", Tetrahedron Asymmetry, Jan. 1, 1995, pp. 245-254, vol. 6, No. 1, Pergamon Press, Ltd., Oxford, GB.
Courilleau et al., "Identification of a Tetrahydroquinoline Analog as a Pharmacological Inhibitor of the cAMP-binding Protein Epac", Journal of Biological Chemistry, Nov. 8, 2012, pp. 44192-44202, vol. 287, No. 53.

* cited by examiner

*Primary Examiner* — Jean Cornet
(74) *Attorney, Agent, or Firm* — Whitham Curtis & Cook, PC (57) ABSTRACT

The invention relates to tetrahydroquinoline derivatives and their use in the treatment and/or the prevention of a disease wherein the Epac protein is involved, such as inflammation, cancer, vascular diseases, kidney diseases, cognitive disorders and cardiac diseases.

13 Claims, 6 Drawing Sheets

TETRAHYDROQUINOLINE DERIVATIVES AND THEIR USE AS EPAC INHIBITORS

The invention relates to tetrahydroquinoline derivatives, their use as Epac inhibitors and their pharmaceutical uses.

Cyclic adenosine 3',5'-monophosphate (cAMP) is a universal second messenger that plays a crucial role in the intracellular signal transduction of various stimuli controlling a wide variety of cellular events including secretion, cell proliferation and differentiation, migration, and apoptosis. The guanine exchange factor (GEF) Epac (Exchange Protein directly Activated by Cyclic AMP) has been shown to contribute to cAMP signalling in many processes (M. Breckler et al., Rap-linked cAMP signaling Epac proteins: compartimentation, functioning and disease implications, Cell. Signal. 23 (2011) 1257-1266).

There are two isoforms of Epac, Epac1 and Epac2, both consisting of a regulatory region binding directly cAMP and a catalytic region that promotes the exchange of GDP (Guanosine diphosphate) for GTP (Guanosine-5'-triphosphate) on the Ras-like small GTPases Rap1 and Rap2 isoforms. In the absence of cAMP, the regulatory region containing the cAMP-binding domain directly interacts with the catalytic region and inhibits its GEF activity. Binding of cAMP to Epac induces large conformational changes within the protein and releases the autoinhibitory effect of the N-terminal region, leading to Rap activation.

The two isoforms of Epac differ in that Epac1 has a single cyclic nucleotide-binding (CNB) domain, whereas Epac2 has two CNB domains, called CNB-A and CNB-B, which are located on both sides of the DEP domain (Dishevelled, Egl-10 and Pleckstrin domain). The additional N-terminal CNB domain in Epac2 has a low affinity for cAMP, and its deletion does not affect the regulation of Epac2 in response to agonists (J. de Rooij, H. Rehmann, M. van Triest, et al., Mechanism of regulation of the Epac family of cAMP-dependent RapGEFs, J. Biol. Chem. 275 (2000) 20829-20836).

Epac plays critical roles in various physiological and pathophysiological processes such as memory formation, inflammation and cardiac remodelling (J. M. Enserink, et al., A novel Epac-specific cAMP analog demonstrates independent regulation of Rap1 and ERK, Nat. Cell Biol. 4 (2002) 901-906; Breckler et al., 2011). Therefore, there is a need to provide Epac antagonists. There is also a need to provide compounds that inhibit downstream effectors such as Rap 1 and Ras following the activation of Epac by Epac agonists. There is also a need to provide Epac antagonists that can be used for the prevention and/or the treatment of diseases where Epac is involved such as inflammation, cancer, vascular diseases, kidney diseases, cognitive diseases and cardiac diseases.

The aim of the invention is to provide novel Epac antagonists.

Another aim of the invention is to provide novel Epac antagonists that inhibit downstream effectors of Epac, even when Epac has been previously activated by agonists.

Another aim of the present invention is to provide novel Epac antagonists which can be useful for the prevention and/or the treatment of inflammation, cancer, vascular diseases, kidney diseases, cognitive diseases and cardiac diseases.

The present invention thus relates to a compound having formula (I):

wherein:
R9 is H or and is the attachment to the nitrogen atom of the tetrahydroquinoline;

R1, R2, R3, R4 and R8 are independently chosen from the group consisting of:
H, $(C_1-C_{10})$alkyl, $(C_3-C_{10})$cycloalkyl, $(C_6-C_{10})$aryl, $(C_1-C_6)$alkylene-$(C_6-C_{10})$aryl and $(C_3-C_{10})$heteroaryl; said aryl and heteroaryl groups being possibly substituted by at least one substituent chosen from OH, $NH_2$, $NO_2$, $(C_1-C_6)$alkyl and halogen;

R5 is an halogen atom;
R6 and R7 are independently chosen from the group consisting of H and halogen atoms;

or its pharmaceutically acceptable salts, hydrates or hydrated salts or its polymorphic crystalline structures, racemates, diastereomers or enantiomers,
for its use in the treatment and/or the prevention of a disease wherein the Epac protein is involved.

The inventors have surprisingly discovered that tetrahydroquinoline derivatives inhibit the Epac protein. This inhibition leads to the inhibition of the Epac-induced Rap1 and Ras activation. Even more surprising, tetrahydroquinoline derivatives inhibit Epac downstream effectors Rap1 and Ras following Epac activation by Epac agonists.

Moreover, it has been shown that these tetrahydroquinoline derivatives are pharmacological inhibitors of Epac biological function, as they block an Epac1-dependent biological process, the cardiac myocyte hypertrophy signalling. Previous studies demonstrated that, in response to a prolonged β-AR (beta adrenergic receptors) stimulation, Epac induced cardiac myocyte hypertrophy (Morel E; et al., cAMP-binding protein Epac induces cardiomyocyte hypertrophy Circ Res. 2005 Dec. 9; 97(12):1296-304. Epub 2005 Nov. 3; Métrich M. et al., Epac mediates beta-adrenergic receptor-induced cardiomyocyte hypertrophy. Circ Res. 2008 Apr. 25; 102(8):959-65. doi: 10.1161/CIRCRESAHA.107.164947. Epub 2008 Mar. 6.).

In one embodiment, the compounds of formula (I) are Epac1 inhibitors. In another embodiment, the compounds of formula (I) are Epac1 selective inhibitors. In one embodiment, Epac1 selective inhibitors are compounds which exhibit an inhibitory effect on the Epac1 isoform. More particularly, they generally exhibit an inhibitory effect on Epac1 and moderate or no inhibitory effect on Epac2 isoform.

By "selective Epac1 inhibitor" it may be understood the ability of the Epac1 inhibitors to affect the particular Epac1 isoform, in preference to the other isoform Epac2. The Epac1 selective inhibitors may have the ability to discriminate between these two isoforms, and so affect essentially the Epac1 isoform.

In one embodiment, they may exhibit a ratio of inhibition of Epac1 versus Epac2 of at least 10 folds. In one embodiment, the compounds of formula (I) do not inhibit the protein kinase A (also called PKA). In one embodiment, the compounds of formula (I) are not AMPc competitive inhibitors.

The term "inhibitor" is to be understood as "antagonist".

By "a disease wherein the Epac protein is involved" is meant a disease wherein the Epac protein is expressed or over-expressed, and/or mutated.

The term "$(C_1-C_{10})$alkyl" means a saturated or unsaturated aliphatic hydrocarbon group which may be straight or branched having 1 to 10 carbon atoms in the chain. Preferred alkyl groups have 1 to 4 carbon atoms in the chain, preferred alkyl groups are in particular methyl or ethyl groups. "Branched" means that one or lower alkyl groups such as methyl, ethyl or propyl are attached to a linear alkyl chain.

The term "$(C_1-C_6)$alkylene-" means a saturated or unsaturated aliphatic hydrocarbon divalent radical which may be straight or branched having 1 to 6 carbon atoms in the chain. For example, a preferred $(C_1-C_6)$alkylene-$(C_6-C_{10})$aryl is a benzyl group.

By "$(C_3-C_{10})$cycloalkyl" is meant a cyclic, saturated hydrocarbon group having 3 to 10 carbon atoms, in particular cyclopropyl or cyclohexyl groups.

The term "$(C_6-C_{10})$aryl" refers to an aromatic monocyclic, bicyclic, or tricyclic hydrocarbon ring system wherein any ring atom capable of substitution may be substituted by a substituent. Examples of aryl moieties include, but are not limited to, phenyl.

The term "$(C_3-C_{10})$heteroaryl" refers to an aromatic monocyclic, bicyclic, or tricyclic hydrocarbon ring system, wherein any ring atom capable of substitution may be substituted by a substituent and wherein one or more carbon atom(s) are replaced by one or more heteroatom(s) such as nitrogen atom(s), oxygen atom(s) and sulphide atom(s); for example 1 or 2 nitrogen atom(s), 1 or 2 oxygen atom(s), 1 or 2 sulphide atom(s) or a combination of different heteroatoms such as 1 nitrogen atom and 1 oxygen atom. Preferred heteroaryl groups are pyridyl, pyrimydyl and oxazyl groups.

The term "halogen" refers to the atoms of the group 17 of the periodic table and includes in particular fluorine, chlorine, bromine, and iodine atoms, more preferably fluorine, chlorine and bromine atoms.

By "tetrahydroquinoline" it is understood the following group:

The compounds herein described may have asymmetric centers. Compounds of the present invention containing an asymmetrically substituted atom may be isolated in optically active or racemic forms. It is well-known in the art how to prepare optically active forms, such as by resolution of racemic forms or by synthesis from optically active starting materials. All chiral, diastereomeric, racemic forms and all geometric isomeric forms of a compound are intended, unless the stereochemistry or the isomeric form is specifically indicated. In an embodiment, the carbon atom referred to with (*) in the formula (I) with R2 to R9 as defined above may be (R) or (S):

In an embodiment it is (R). In a particular embodiment, the enantiomeric form (R) of the compound of formula (I) is preferred and more particularly the following enantiomeric form:

In another embodiment, the (R)-enantiomeric form of the compound of formula (I) is a more potent cAMP antagonist than racemic and (S)-enantiomeric form of the compound of formula (I). In one embodiment, the (R)-enantiomeric form of the compound of formula (I) is a selective inhibitor of Epac1. Said (R)-enantiomeric form may inhibit the GEF activity of Epac1 with 10-times more efficiency than the (S)-enantiomeric form.

The term "pharmaceutically acceptable salt" refers to salts which retain the biological effectiveness and properties of the compounds of the invention and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

In a particular embodiment, the compounds of the invention have the following formula:

that is in formula (I), R9 is

In a particular embodiment, the compounds of the invention have the following formula (II):

wherein
R1, R2, R3, R4 and R8 are independently chosen from the group consisting of:
H, $(C_1-C_{10})$alkyl, $(C_3-C_{10})$cycloalkyl, $(C_6-C_{10})$aryl, $(C_1-C_6)$alkylene-$(C_6-C_{10})$aryl and $(C_3-C_{10})$heteroaryl; said aryl and heteroaryl groups being possibly substituted by at least one substituent chosen from OH, $NH_2$, $NO_2$, $(C_1-C_6)$alkyl and halogen;
R5 is an halogen atom;
R6 and R7 are independently chosen from the group consisting of H and halogen atoms;
or its pharmaceutically acceptable salts, hydrates or hydrated salts or its polymorphic crystalline structures, racemates, diastereomers or enantiomers,
for its use in the treatment and/or the prevention of a disease wherein the Epac protein is involved.

In a particular embodiment, in formula (II) as defined above R1 is H.

The above embodiments refer either to formula (I) or to formula (II).

In a particular embodiment, R2 is H or a $(C_1-C_{10})$alkyl.

In a particular embodiment, R2 is a $(C_1-C_{10})$alkyl. Preferably, R2 is a $(C_1-C_4)$alkyl.

More preferably, R2 is a methyl group. In another embodiment, R2 is H. Preferably, R2 is H or a methyl group.

In a particular embodiment, R3 is H.
In another embodiment, R4 is H.
In another embodiment, R8 is H.
In one embodiment, R3, R4 and R8 are H.
In a particular embodiment, the $(C_3-C_{10})$heteroaryl group is chosen from the group consisting of pyridyl, pyrimydyl and oxazyl groups.

In another embodiment, the $(C_6-C_{10})$aryl group is a phenyl group.

In another embodiment, the $(C_1-C_6)$alkylene-$(C_6-C_{10})$aryl is a benzyl group.

In a particular embodiment, R5 is chosen from the group consisting of F, Cl, Br and I. Preferably, R5 is Br.

In a particular embodiment, R6 is chosen from the group consisting of H, F, Cl, Br and I.

In a particular embodiment, R6 is chosen from the group consisting of F, Cl, Br and I.

In another embodiment, R6 is F. In another embodiment R6 is H. Preferably, R6 is H or F.

In a particular embodiment, R7 is chosen from the group consisting of H, F, Cl, Br and I.

In a particular embodiment, R7 is chosen from the group consisting of F, Cl, Br and I. In another embodiment, R7 is Br. In another embodiment, R7 is H. Preferably, R7 is H or Br.

In a preferred embodiment, R1 is H and R5 is Br.
In another preferred embodiment, at least two of R5, R6 and R7 are halogen.

The above mentioned particular embodiments can be combined with each other.

Some specific compounds for the use as defined above have the following formulae:

named herein CE3F4, a)

-continued e)

f)

g)

and

More particularly, some specific compounds for the use as defined above have the following formulae:

h)

-continued a)

e)

f)

In one embodiment, the compound of formula (I) is:

The present application also describes the following compounds:

b)

c)

and d)

The invention also relates to a compound having one of the following formulae:

e)

f)

and g)

Preparation of the Compounds of Formula (I):

The compounds of formula (I) can be synthesized according to previously published methods in P. Bouyssou et al., J. Heterocyclic Chem., 29, 895, 1992. Methods of preparation of the compounds of formula (I) are well-known.

The present invention also relates to a pharmaceutical composition, comprising a compound having formula (I) for its use as defined above, in association with at least one pharmaceutically acceptable excipient.

The present invention also relates to a drug, comprising a compound having formula (I) for its use as defined above.

While it is possible for the compounds having formula (I) to be administered alone, it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and possibly other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The invention relates to a compound having formula (I) as defined above, for its use for the treatment and/or the prevention of inflammation, cancer, vascular diseases including atherogenesis, atherosclerosis and postangioplasty restenosis, kidney diseases including diabetic nephropathy, cognitive disorders and cardiac diseases.

The invention also relates to the use of a compound having formula (I) as defined above, for the preparation of a medicament for the treatment and/or the prevention of inflammation, cancer, vascular diseases including atherogenesis, atherosclerosis and postangioplasty restenosis, kidney diseases including diabetic nephropathy, cognitive disorders and cardiac diseases.

By "inflammation" is meant phenomena by which the human body defends itself against aggression and which can manifest itself in various symptoms such as pain, swelling, heat or redness of the skin.

By the term "cancer" is meant solid tumors and/or disseminated hematological cancers and/or their metastasis. The terms "metastasis" or "metastatic diseases" refer to secondary tumors that are formed by cells from a primary tumor which have moved to another localization. The term "hematological cancers" refers to types of cancer that affect blood, bone marrow, and lymph nodes such as myelomas, lymphomas or leukemias.

Cognitive disorders are a category of mental health disorders that primarily affect learning, memory, perception, and problem solving, and include amnesia, dementia, and delirium, more particularly Alzheimer's disease.

Cardiac diseases more specifically point out cardiac hypertrophy, cardiac arrhythmias, valvulopathies, diastolic dysfunction, chronic heart failure, ischemic heart failure, myocarditis, hypertrophic and dilated cardiomyopathies. It has to be noted that besides Rap1, Epac1 has been shown to activate the small GTPase H-Ras in different cell types including primary cardiomyocytes (Keiper et al., 2004; Métrich et al., 2008; Métrich et al., 2010a, 2010b; Schmidt et al., 2001).

The invention thus also relates to a compound of formula (I) as defined above, for its use for the treatment and/or the prevention of cardiac diseases which are selected from the group consisting of cardiac hypertrophy, cardiac arrhythmias, valvulopathies, diastolic dysfunction, chronic heart failure, ischemic heart failure, myocarditis, hypertrophic and dilated cardiomyopathies, preferably cardiac hypertrophy.

The invention also relates to a method of prevention and/or treatment of a disease wherein the Epac protein is involved, said method comprising the administration of a pharmaceutical acceptable amount of a compound of formula (I) as defined above to a patient in need thereof. Preferably, the present invention relates to a method of prevention and/or treatment of inflammation, cancer, vascular diseases including atherogenesis, atherosclerosis and postangioplasty restenosis, kidney diseases including diabetic nephropathy, cognitive diseases and cardiac diseases, said method comprising the administration of a pharmaceutical acceptable amount of a compound of formula (I) as defined above to a patient in need thereof.

More particularly, the invention relates to a method of prevention and/or treatment of cardiac hypertrophy, cardiac arrhythmias, valvulopathies, diastolic dysfunction, chronic heart failure, ischemic heart failure, myocarditis, hypertrophic and dilated cardiomyopathies, said method comprising the administration of a pharmaceutical acceptable amount of a compound of formula (I) as defined above to a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

DESCRIPTION OF THE FIGURES

FIGS. 3A, 3B and 3C show the inhibitory activity of CE3F4 on Epac-induced Ras activation.

FIGS. 4A and 4B show that CE3F4 prevents Epac-induced cardiac remodeling.

FIG. 6A shows the initial velocity of GDP exchange catalyzed by Epac1 (black bars), Epac2(AB) (empty bars), and Epac2(B) (hatched bars) incubated with 50 μM racemic CE3F4 and with 50 μM 007 or 300 μM cAMP, as indicated below the x-axis.

FIG. 6B shows Epac1 (black circles) or Epac2B (empty squares) activated by 300 μM cAMP, and the initial velocity of GDP exchange in the presence of increasing concentrations of (R)-CE3F4.

FIG. 6C shows the initial velocity of GDP exchange catalyzed by Epac1 (hatched bars) or Epac2(B) (black bars) measured in the presence of 30 μM racemic CE3F4 or compounds a) from h), and 300 μM cAMP as the agonist. Results are expressed relative to the control values measured in the absence of inhibitor, which were set at 100%. p<0.01% for global comparison of Epac2(B) and Epac1 (Wilcoxon matched-pair signed rank test). p<5% or less for comparison of Epac2(B) and Epac1 to be inhibited by each compound (one-tailed Student's t-test).

The following examples represent some specific embodiments of the invention and can not be considered as limiting.

EXAMPLES

In the following examples:

"CE3F4" refers to the specific compound having the following formula:

CE3F4 and related compounds a), b), c), d), g), and h) were synthesized according to methods described in P. Bouyssou, et al., Synthesis of 7- and 5,7-substituted-6-fluoro-2-methyl-1,2,3,4-tetrahydroquinolines: convenient precursors of quinolone antibacterial agents, J. Heterocyclic Chem. 29 (1992) 895-898.

compound f) was synthesized from 6-fluoroquinoline by reduction and formylation of this compound to give 6-fluoro-1-formyl-1,2,3,4-tetrahydroquinoline, which was then brominated to give compound f).

compound e) was synthesized from 3,5-dibromoaniline by a Skraup synthesis to give 5,7-dibromoquinaldine followed by reduction of nitrogen-containing ring and formylation of nitrogen in position 1.

The (R)- and (S)-enantiomers of CE3F4 were derived from the (R)- and (S)-enantiomers of 6-fluoro-2-methyl-1,2,3,4-tetrahydroquinoline (6-FTHQ). (R)- and (S)-6-FTHQ were obtained according to methods described in J. F. Gerster, et al., Synthesis, absolute configuration, and antibacterial activity of 6,7-dihydro-5,8-dimethyl-9-fluoro-1-oxo-1H,5H-benzo[ij]quinolizine-2-carboxylic acid, J. Med. Chem. 30 (1987) 839-843 and were then formylated and brominated to give, respectively, (R)-CE3F4 and (S)-CE3F4.

The mass spectra and nuclear magnetic resonance of these compounds were identical to those reported previously for racemic CE3F4 (Bouyssou P., 1990. Contribution à l'étude des quinolones carboxyliques de structure type Benzo[i,j] Quinolizine, relation structure activité. Ph.D. Thesis. Orléans University, France). Optical rotation measurements were performed at 589 nm, 20° C. and c=10 mg/ml in chloroform, with an accuracy of ±1°, using a Perkh Elmer model 341 polarimeter. (R)-CE3F4 is levorotatory with $[\alpha]D=-12\pm1°$, while (S)-CE3F4 is dextrorotatory with $[\alpha]D=+11\pm1°$.

"Compound 007" refers to the Epac agonist, 8-(4-chlorophenylthio)-2'-O-methyladenosine-3',5'-cyclic monophosphate, obtained from Biolog, Bremen, Germany. "Compound 007", is a cAMP analog which activates Epac, but not PKA.

"Compound 009" refers to 8-(4-chlorophenylthio)-guanosine-3',5'-cyclic monophosphate, obtained from Biolog, Bremen, Germany.

"Sp-007" refers to a membrane-permeant Epac agonist, Sp-8-pCPT-2'-O-Me-cAMPS (Christensen et al., 2003).

Isoprenaline (also called "Iso") was obtained from Sigma-Aldrich.

BODIPY FL 2'-(or -3')-O—(N-(2-aminoethyl)urethane), bis(triethylammonium) salt (Bodipy-GDP) was obtained from Invitrogen.

Example 1: Kinetic Characteristics of Epac Inhibition by CE3F4

The effects of CE3F4 on the exchange activity of Epac-1 were studied as follows.

Figure 1:
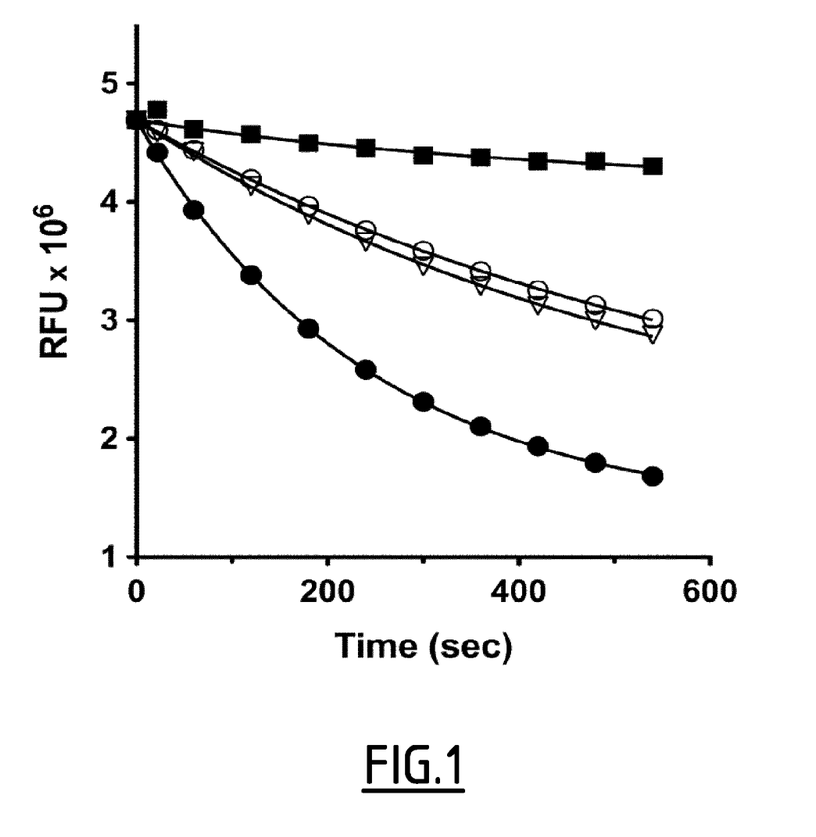
FIG. 1 shows the inhibitory activity of CE3F4 on the exchange activity of Epac1. Epac1 nucleotide exchange activity was measured as a function of time (in seconds) in the absence of compound 007 (curve with squares) or in the presence of 2 μM of compound 007, either alone (curve with closed circles) or with 25 μM of compound 009 (curve with triangles) or with 20 μM of CE3F4 (curve with open circles).

Protocol:
Epac1 nucleotide exchange activity was measured:
in the absence of compound 007,
or in the presence of 2 µM of compound 007, either alone or with 25 µM of compound 009,
or with 20 µM of CE3F4.
Variations of RFU (Relative Fluorescence Units) were studied as a function of time and fitted to single exponentials. Reported values are mean±SEM (n=3). (see Materiel and Methods).

Results:
FIG. 1 shows that a single dose of CE3F4 inhibited the exchange reaction induced by Epac1 plus 007 (2 µM) to an extent similar to the inhibitory effect of 009 at 25 µM.

Example 2: Effects of CE3F4 on Epac Downstream Effectors in Cultured Cells

1) Effects of CE3F4 on Epac1-Induced Rap1 Activation:
The ability of CE3F4 to block Epac1-induced Rap1 activation in cultured HEK293 cells was tested according to the following experiment.

Protocol:
HEK293 cells were transfected with either pcDNA3 control vector or Epac1 (see FIG. 2A).

Figure 2:
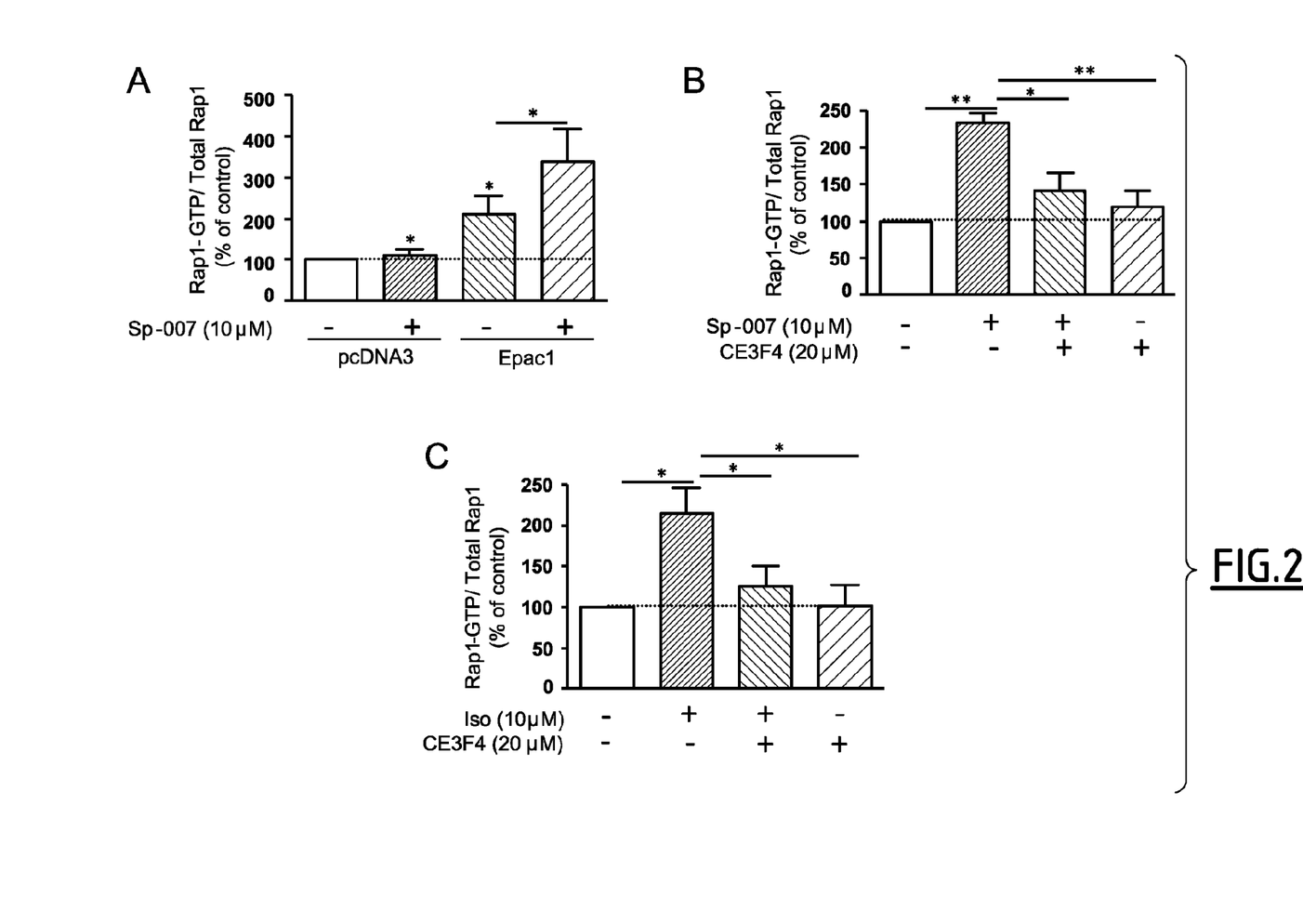
FIGS. 2A, 2B and 2C show the inhibitory activity of CE3F4 on Epac-induced Rap1 activation.

HEK293 cells were transfected with Epac1 and 24 h after transfection, cells were preincubated or not with CE3F4 for 30 min and were then treated or not with Sp-007 (10 µM) for 10 min (see FIG. 2B).

HEK293 cells overexpressing β1AR (Beta-1 adrenergic receptors) and transfected with Epac1 were pretreated or not with CE3F4 and stimulated or not with Iso (10 µM) for 10 min (see FIG. 2C).

Amounts of Rap1-GTP were determined by pull-down assays (see Material and Methods). The bar graph represents the mean±S.E.M. of 5 (FIGS. 2A, 2B) or 3 (FIG. 2C) independent experiments. Results are expressed as the percentage of unstimulated control cells.

Results:
FIG. 2A shows that with the vector control, even in the presence of Sp-007, the ratio Rap1-GTP/Total Rap1 is lower than for cells transfected with Epac1, and that in presence of Sp-700, the cells transfected with Epac1 had higher level of Rap1-GTP. Sp-007 induced a robust activation of Rap1 in cells overexpressing Epac1 compared to control cells transfected with the empty vector.

CE3F4 (20 µM) prevented the increase in the amount of Rap1-GTP following 10 µM of Sp-007 treatment (FIG. 2B). Similarly, CE3F4 decreased Epac1-induced Rap1 activation following stimulation of $β_1$-adrenergic receptor ($β_1$-AR) by isoprenaline (Iso, 10 µM) (FIG. 2C)

2) Effects of CE3F4 on Epac1-Induced H-Ras Activation:
The effects of CE3F4 to prevent Epac1-induced H-Ras activation was determined by extraction of GTP-loaded H-Ras from cell lysates with the immobilized Ras-binding domain of Raf1.

Figure 3:
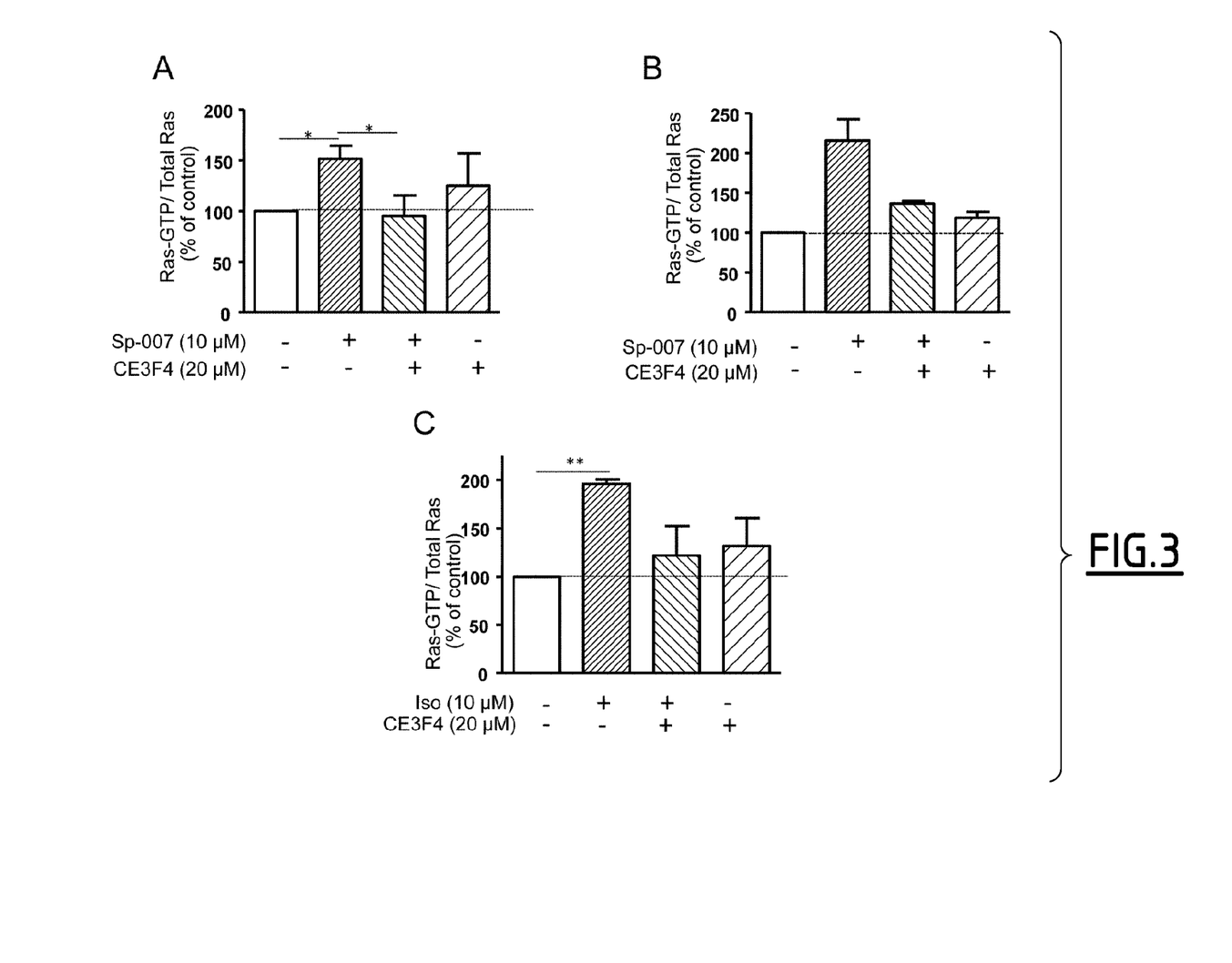
FIG. 3A shows the inhibitory activity of CE3F4 on Epac-induced Ras activation in HEK293 cells.
FIG. 3B shows the inhibitory activity of CE3F4 on Epac-induced Ras activation in rat neonatal cardiac myocytes.
FIG. 3C shows the inhibitory activity of CE3F4 on Epac-induced Ras activation in HEK293 cells overexpressing $\beta_1$-AR.

Protocol:
HEK293 cells (FIG. 3A) or rat neonatal cardiac myocytes (FIG. 3B) were transfected with Epac1. 24 h after transfection, cells were preincubated or not with CE3F4 for 30 min and were then treated or not with Sp-007 (10 µM) for 10 min. In FIG. 3C, HEK293 cells overexpressing $β_1$-AR and transfected with Epac1 were pretreated or not with 20 μM of CE3F4 for 30 min and stimulated or not with Iso for 10 min. Amounts of H-Ras-GTP were determined by pull-down assays. The bar graph represents the mean±S.E.M. of 5 (FIG. 3A) or 2 (FIG. 3B, 3C) independent experiments. Results are expressed as the percentage of unstimulated control cells.

Results:

As observed for Rap1, the amount of Ras-GTP induced by either Sp-007 or Iso was decreased in the presence of CE3F4 in HEK293 and primary rat cardiac myocytes (FIGS. 3A, 3B and 3C).

Conclusion:

Altogether these data show that CE3F4 is efficient in preventing Epac-induced Rap1 and Ras activation in cultured cells.

Example 3: CE3F4 Prevents Epac-Induced Cardiac Myocyte Hypertrophy

The potential biological effects of CE3F4 on Epac-induced cardiac myocyte growth following β-AR stimulation were investigated as follows.

ANF (Atrial Natriuretic Factor) is a marker of myocyte hypertrophy.

NFAT is a nuclear factor involved in Epac pro-hypertrophic signalling (see Métrich et al., 2010b).

ANF and NFAT promoters were fused to the Firefly luciferase gene (ANF-Luc) (NFAT-Luc) to detect ANF and NFAT by Firefly Luciferase assay (see Materiel and Methods).

Protocol:

A) Iso-Induced ANF-Luc Transcriptional Activation is Blocked by CE3F4:

Rat neonatal cardiomyocytes were cotransfected with ANF-Luc and Epac1 or empty vector pcDNA3 as control. One day after transfection, cells were pretreated or not with CE3F4 (20 μM) for 30 min and stimulated or not with Iso (10 μM) for 8 h. Cells were then assayed for Luciferase activity.

B) Iso-Induced NFAT-Luc Transcriptional Activation is Blocked by CE3F4:

Neonatal cardiomyocytes were transfected with NFAT-Luc. One day later cells were pretreated or not with CE3F4 (20 μM) for 30 min and stimulated or not with Iso (10 μM) for 8 h. The day after, cells were assayed for Luciferase activity.

Results were normalized to control for each experiment, and were expressed as means±S.E.M of at 4 (FIG. 4A) or 5 (FIG. 4B) independent experiments performed in triplicates.

Figure 4:
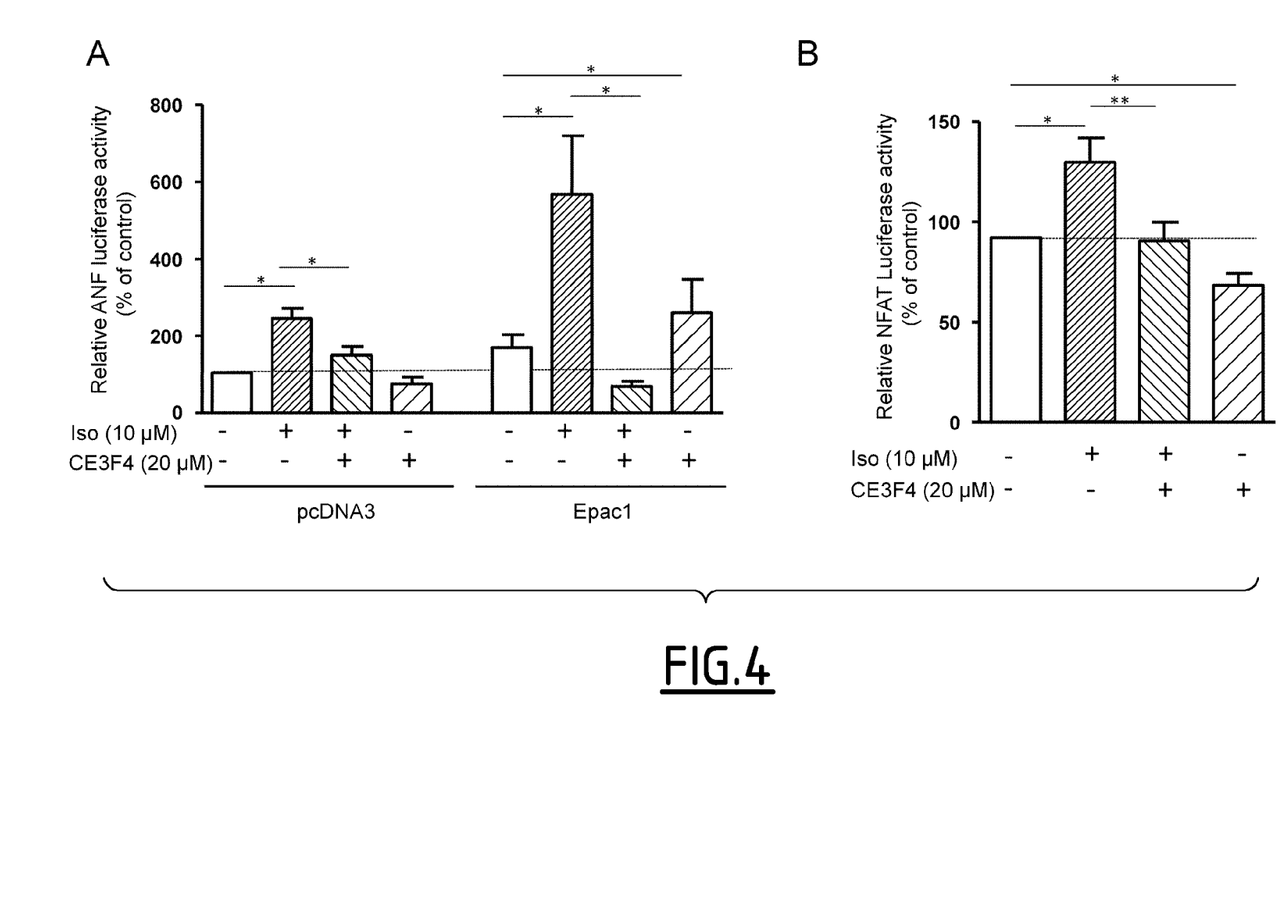
FIG. 4A shows the inhibition of the Iso-induced ANF-Luc transcriptional activation by CE3F4.
FIG. 4B shows the inhibition of the Iso-induced NFAT-Luc transcriptional activation by CE3F4.

Results:

Iso increased ANF as shown in FIG. 4A. The effect of Iso was boosted in cardiomyoctes overexpressing Epac (FIG. 4A). Importantly, treatment of cardiac myocytes with CE3F4 significantly inhibited Iso-induced ANF-Luc gene transcriptional activity (FIG. 4A).

Consistent with this finding, CE3F4 prevented Iso-induced NFAT transcriptional activity (FIG. 4B).

Conclusion:

These data indicate that CE3F4 is a pharmacological inhibitor of Epac biological function.

Example 4: (R)-CE3F4 is a More Potent Enantiomer that Antagonizes Epac1 Activation by cAMP than the (S)-CE3F4

Figure 5:
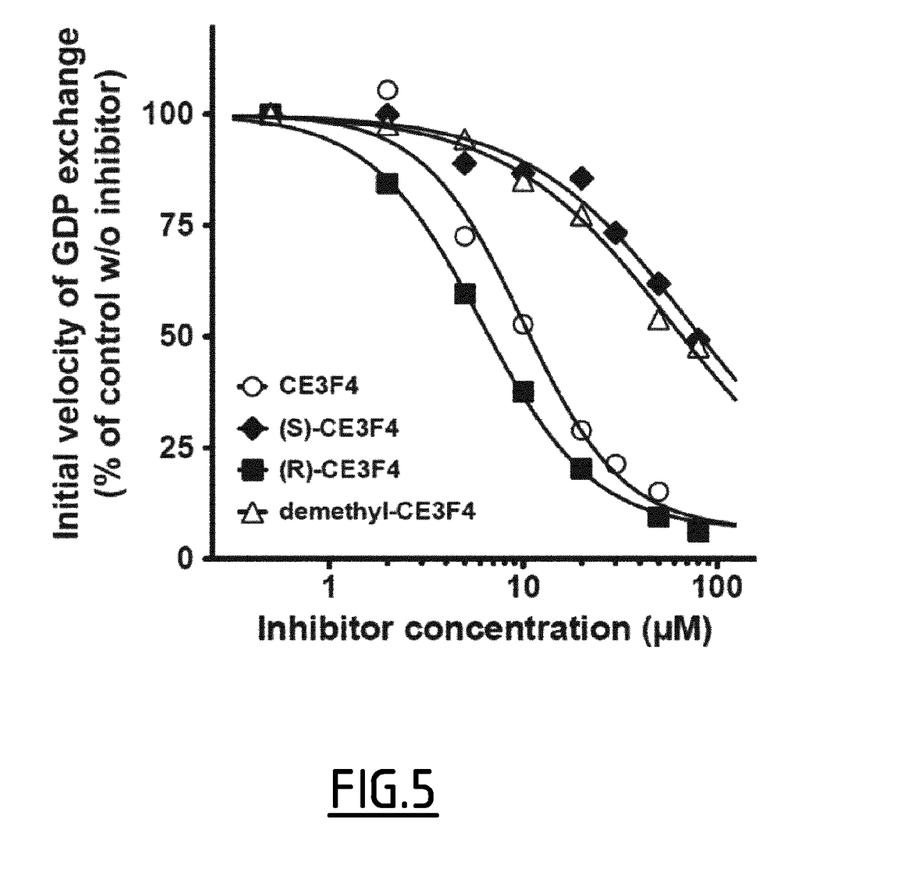
FIG. 5 shows initial velocities of GEF activity of Epac1 activated by 20 μM of 007 in the presence of increasing concentrations of racemic CE3F4 (empty circles), (R)-CE3F4 (black squares), (S)-CE3F4 (black diamonds), and compound f) (empty triangles).

FIG. 5 shows a representative dose-response inhibition assay in which the GEF activity of 007-activated Epac1 toward Rap1 was measured in the presence of increasing concentrations of racemic CE3F4 or of its individual enantiomers (R)-(−)-CE3F4 and (S)-(+)-CE3F4. The dose-response curve for the (R)-enantiomer is left-shifted relative to that obtained with the racemate and with the (S)-enantiomer, showing that the (R)-(−)-CE3F4 is a more potent Epac inhibitor.

The compound f) was also tested: the dose-response curve was not significantly different (F test) from the one obtained with (S)-CE3F4. Each experimental point is the mean of initial velocity values computed from triplicate time-course experiments.

The $IC_{50}$ values for the racemate, enantiomers and compound f) were determined several times independently:

|  | Mean EC50 (μm) | SD | n | p |
| --- | --- | --- | --- | --- |
| CE3F4 | 10.7 | 1.4 | 6 | <1% |
| (R)-CE3F4 | 5.8 | 0.8 | 9 | <1% |
| (S)-CE3F4 | 56 | 7 | 8 | NS |
| Compound f) | 50 | 5 | 4 | NS |

(R)-CE3F4 inhibited Epac1 GEF activity with an $IC_{50}$ which was about 2-fold smaller than that obtained with the racemic CE3F4, and about 10-fold smaller that the $IC_{50}$ values of (S)-CE3F4 and compound f). $IC_{50}$ values were computed using Graphpad Prism, according to a four-parameters dose-response model. (C) Mean±SD of n=4 to 9 independent determinations of $IC_{50}$ values for each inhibitor.

Example 5: (R)-CE3F4 and its Analogs Differentially Inhibit Epac1 and Epac2

Epac1, Epac2(AB) that possesses both the CNB-A and the CNB-B domains, or Epac2(B) that is deleted of its CNB-A domain, were activated by saturating concentrations of either 007 (50 μM) or cAMP (300 μM).

Figure 6:
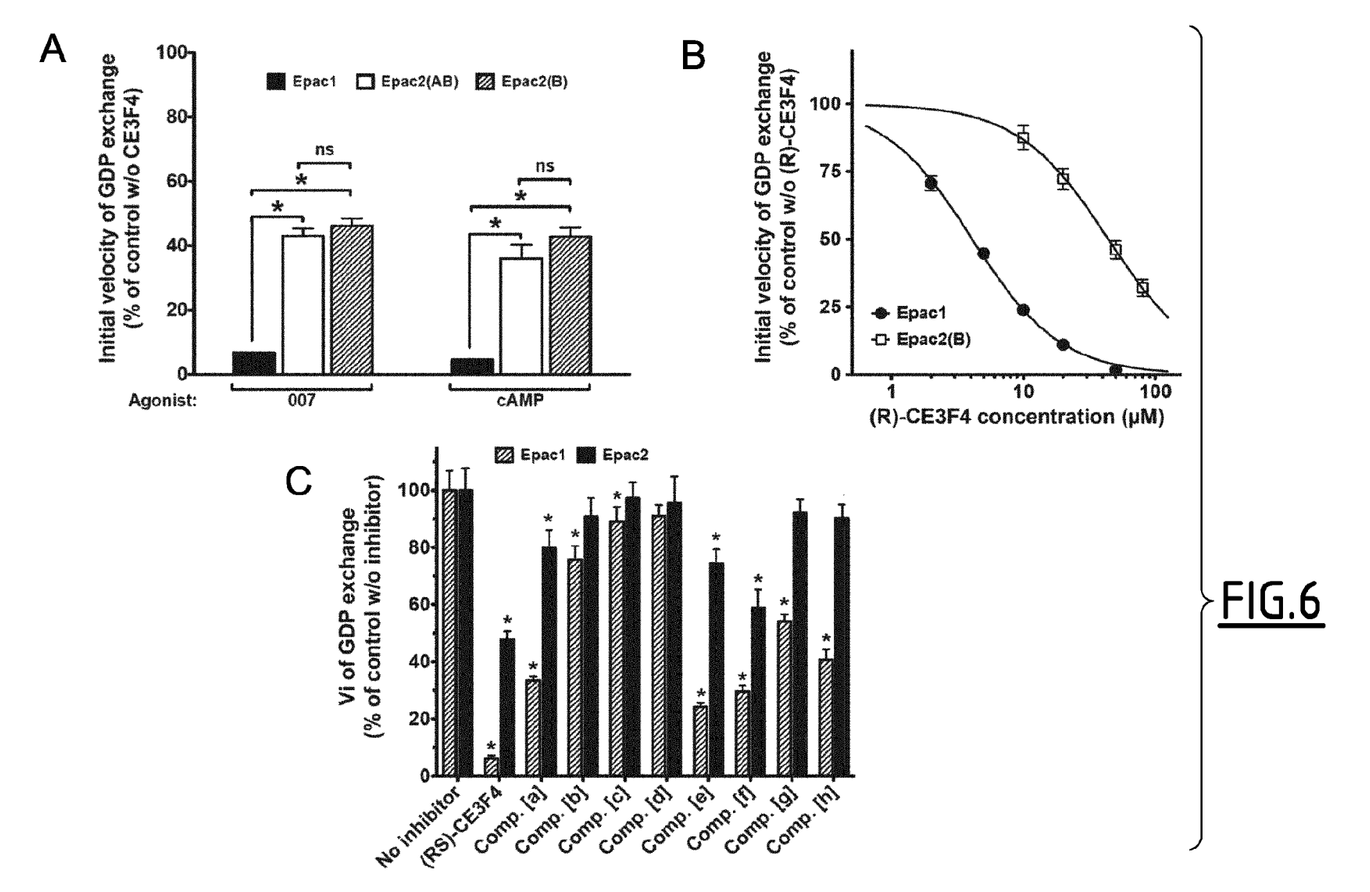
FIG. 6 shows the initial velocity of GDP exchange catalyzed by Epac1, Epac2(AB), or Epac2(B), in the presence or absence of agonists and of inhibitory compounds. The agonist-dependent activity was obtained by subtraction of the constitutive GDP exchange activity, measured in the presence of Epac proteins but in the absence of agonists and inhibitors.

FIG. 6A shows that, whatever the agonist used, the GEF activity of Epac1 was much more inhibited by 50 μM of racemic CE3F4 than the GEF activity of either Epac2(AB) or Epac2(B). On the other hand, there was no significant difference in the inhibitory effects of racemic CE3F4 on the GEF activity of Epac2(AB) or of Epac2(B). (R)-CE3F4 was then used to study the concentration-dependent inhibition of the GEF activities of Epac1 and Epac2(B) activated by cAMP (300 μM). Results are expressed as the % of the initial velocity of GDP exchange measured in the absence of racemic CE3F4. *, p<1%; ns (not significant), p>5% by two-tailed Student's t-test.

FIG. 6B shows that the dose-response curve obtained with Epac2(B) is strongly right-shifted relative to that obtained with Epac1. From two independent dose-response experiments such as the one shown in FIG. 6B, the mean $IC_{50}$ of (R)-CE3F4 was 4.2 μM for Epac1 and 44 μM for Epac2(B). Results are expressed as the % of the initial velocity of GDP exchange measured in the absence of (R)-CE3F4. p<0.1% by comparison of fits ($IC_{50}$) based of the extra sum-of square F test (Graphpad Prism).

FIG. 6C: cAMP-activated Epac1 and Epac2(B) were compared for their ability to be inhibited by several CE3F4 structural analogs. All of them are in the racemic form, except for the compound f). FIG. 6C shows the results of a representative experiment, expressed as the relative inhibitory potencies of the various analogs (30 μM), measured in the presence of cAMP (300 μM) as the agonist.

Compounds a), e) and f) showed antagonistic properties toward both Epac isoforms even if they were weaker cAMP antagonists toward Epac2(B) than toward Epac1 by two-tailed Wilcoxon matched-pair signed rank test (p value<1%,). Compounds g) and h) showed antagonistic properties toward Epac1.

The stronger antagonist of Epac1 and Epac2(B) activation by cAMP was CE3F4 itself. A dose-response study (not shown) indicated that the $IC_{50}$ of racemic CE3F4 was 11 μM for Epac1 and 66 μM for Epac2(B) when they were activated by 300 μM cAMP.

Comparative compounds b), c) and d), which are not encompassed by the formula (I) of the compounds of the invention, showed no significant inhibitory activity on both Epac isoforms.

Material and Methods:

Measurement of In Vitro Activation of Epac1

Method used to determine Epac1 exchange activity:

Concerning FIG. 1, a "multipoint" (time-course) method was used. All components except the agonist (007) were mixed in a well and the exchange activity of Epac1 was initiated by injection of the agonist. GST-Rap1 was pre-loaded with a fluorescent derivative of GDP, and the Epac1-catalyzed nucleotide exchange was measured using a large excess of non-fluorescent GDP, by taking advantage of the spectroscopic difference between free and Rap1-bound fluorescently labeled GDP. The principle of the method is similar to that reported in particular by Van den Berghe et al. (1997; Oncogene 15, 845), except that Bodipy FL-labeled GDP (bGDP) was used here, rather than 2',3'-bis(O)—N-methylanthraniloyl-GDP (mant-GDP).

To determine Epac1 exchange activity, 200 nM of purified GST-Rap1A preloaded with bGDP were incubated at 22° C. in exchange buffer (50 mM Tris-HCl, pH 7.5, 50 mM NaCl, 5 mM $MgCl_2$, 5 mM DTE, 5% glycerol, 0.01% NP40), in the presence of 100 nM of purified GST-Epac1, 20 μM of unlabeled GDP, and defined concentrations of compound 007, compound 009 and CE3F4. Experiments were performed in black 384-well plates (Corning Inc. Ref 3573) in a final volume of 30 μL. bGDP fluorescence (Ex=480 nm; Em=535 nm) was measured using a multilabel plate reader (Envision Xcite, Perkin-Elmer).

Method used to measure the amount of either Rap1-GTP or Ras-GTP induced by Epac: see pulldown assay.

Cell Culture:

Cardiac myocytes were isolated as previously described by Wollert and colleagues (1996). HEK293 cells stably expressing the $β_1$-adrenergic receptor ($β_1$-AR) was a gift of Dr. Shenoy (Duke University). HEK293 cells were maintained in MEM with FBS (Foetal Bovine Serum; 10%) and penicillin-streptomycin (1%). All media, sera and antibiotics used in cell culture were purchased from Invitrogen (Cergy Pontoise, France).

Plasmid and Transfection:

The plasmid constructs were generously provided as following:

The rat ANF promoter fused to the Firefly luciferase reporter gene (ANF-Luc) by Dr K. Knowlton, Epac and Rap1 plasmid construct (Epac1$^{WT}$) by Drs J. L. Bos and J. de Gunzburg, respectively. The Firefly luciferase reporter plasmid driven by four NFAT consensus binding sites (NFAT-Luc) was purchased from Stratagene. Transient transfection experiments of HEK cells and primary cardiac myocytes were performed with respectively X-treme GENE 9 reagent (Roche Applied Science) and Lipofectamine 2000 (Invitrogen Life Technologies) in the presence of various amounts of plasmid constructs according to the manufacturer's instructions.

Firefly Luciferase Assay:

Cells were lysed, and luminescence was detected using the Luciferase Assay System (Promega) according to the manufacturer's instructions with Tecan Infinite.

Pull-Down Assay:

Ras and Rap1 pull-down experiments were performed using a GST fusion protein containing respectively the Ras binding domain of Raf1-RBD and the Rap1 binding domain of Ral-GDS as previously described (Métrich et al., 2008). Cells were starved for 1 h before stimulation in MEM free with penicillin-streptomycin (1%). After stimulation, cells were lysed in RIPA buffer (50 mM Tris-HCl, pH 7.5; 500 mM NaCl; 20 mM $MgCl2$; 0.5% deoxycholic acid; 0.1% SDS; 1% Triton X-100; 1 mM PMSF; protease and phosphatase inhibitors) and 500 μg of protein were incubated with either GST-Raf1-RBD (for Ras) or Ral-GDS (for Rap1) coupled to glutathione-Sepharose beads (Amersham Biosciences) for 1 h at 4° C. Beads were then washed three times in washing buffer (50 mM Tris-HCl, pH 7.5; 150 mM NaCl, 20 mM $MgCl_2$, 1% Triton X-100; 0.1 mM PMSF; protease and phosphatase inhibitors). Rap1-GTP or Ras samples and corresponding total lysates were separated on SDS-PAGE gels and transferred onto a polyvinylidene difluoride (PVDF) membrane (Amersham Pharmacia Biotech). Membranes were revealed with Dura kit (Pierce).

Recombinant Protein Expression:

Protein NCBI Reference Sequences for human Epac1 and Epac2 are NP_006096 and NP_008954, respectively. Recombinant human Epac1 (residues 149-881), deleted of its Dishevelled, Egl-10, and Pleckstrin (DEP) domain, and human Rap1A were produced with GST as a fusion tag (D. Courilleau et al., Identification of a tetrahydroquinoline analog as a pharmacological inhibitor of the cAMP-binding protein Epac, J. Biol. Chem. 287 (2012) 44192-44202).

Human Epac2(AB) (amino acids 43-1011) carries both the CNB-A and the CNB-B domains. Human Epac2(B) (amino acids 283-1011) lacks the first 283 amino acids of Epac2. It is therefore deleted of its CNB-A and DEP domains, but retains the CNB-B domain and the full catalytic region. Epac2(AB) was obtained by HindIII/NotI restriction and Epac2(B) was obtained by Ssp1/Not1 restriction of a human Epac2A cDNA (a gift from Ann M Graybiel, Department of Brain and Cognitive Sciences, MIT, Cambridge). Both cDNA fragments were inserted into pET41a (Novagen), expressed in *Escherichia coli* Rosetta 2(DE3) (Novagen), and the GST-tagged fusion proteins were purified by nickel-nitrilotriacetic acid beads (Qiagen), as described in D. Courilleau, et al., Identification of a tetrahydroquinoline analog as a pharmacological inhibitor of the cAMP-binding protein Epac, J. Biol. Chem. 287 (2012) 44192-44202).

Assay of In Vitro GEF Activity:

In vitro GDP exchange catalyzed by Epac was measured using purified recombinant Epac isoforms and Rap1A loaded with Bodipy-GDP, as described in D. Courilleau, et al (above mentioned). The GEF activity of Epac proteins was initiated by injection of the agonist. Stock solutions of CE3F4 and its analogs (12 mM in 100% DMSO) were kept at −20° C. and were diluted in assay buffer (0.67% final DMSO concentration) just before use for GDP exchange assays. The release of Bodipy-GDP was measured in real time as the decay of fluorescence. A single exponential was fit to the time-course data using the Graphpad Prism program. The initial velocity (Vi) of GDP exchange on Rap1 was calculated as described in D. Courilleau et al.).

Statistical Analysis

Examples 1 to 3

All data are expressed as means±standard error of the mean. Differences in quantitative variables were examined by one-way analysis of variance (ANOVA) or paired two-tailed t test. p value<0.05 (*), p value<0.01 () and p value<0.001 (*). All analyses were performed using GraphPad Prism.

Examples 4 and 5

Data are expressed as mean±S.D. Differences in quantitative variables were examined by unpaired one- or two-tailed Student's t test. $EC_{50}$ and $IC_{50}$ values were computed according to a four-parameters dose-response model and compared on the basis of the extra sum-of square F test, using Graphpad Prism. Two-tailed Wilcoxon matched-pair signed rank tests were performed using GraphPad Prism.

The invention claimed is:

1. A method of treatment of a disease, disorder, or condition, or one or more symptoms thereof wherein the Epac protein is involved, said method comprising the administration of a pharmaceutically acceptable amount of a compound of formula (I) to a patient in need thereof:

wherein:
R9 is and is the attachment to the nitrogen atom of the tetrahydroquinoline;
R1, R2, R3, R4 and R8 are independently chosen from the group consisting of:
H and ($C_1$-$C_5$);
R5 is an halogen atom;
R6 and R7 are independently chosen from the group consisting of H and halogen atoms;
or its pharmaceutically acceptable salts, hydrates or hydrated salts, racemates, diastereomers or enantiomers,
wherein said compound of formula (I) is a selective inhibitor of EPAC1, and
wherein the disease, disorder, or condition is selected from cardiac diseases, wherein said cardiac diseases are selected from the group consisting of cardiac hypertrophy, cardiac arrhythmias, valvulopathies, diastolic dysfunction, chronic heart failure, ischemic heart failure, myocarditis, hypertrophic and dilated cardiomyopathies.

2. The method according to claim 1, wherein in the compound of formula (I) R1 is H.

3. The method according to claim 1, wherein in the compound of formula (I) R2 is H or a ($C_1$-$C_5$)alkyl.

4. The method according to claim 1, wherein in the compound of formula (I) R2 is H or a methyl group.

5. The method according to claim 1, wherein in the compound of formula (I) R5 and/or R6 is selected from the group consisting of F, Cl, Br and I.

6. The method according to claim 1, wherein in the compound of formula (I) R6 is H or F.

7. The method according to claim 1, wherein in the compound of formula (I) R7 is selected from the group consisting of H, F, Cl, Br and I.

8. The method according to claim 1, wherein in the compound of formula (I) R7 is H or Br.

9. The method according to claim 1, wherein in the compound of formula (I) R1 is H and R5 is Br.

10. The method according to claim 1, wherein in the compound of formula (I) at least two of R5, R6 and R7 are halogen.

11. The method according to claim 1, wherein the compound of formula (I) has one of the following formulae:

-continued a)

e)

f)

and

-continued g)

12. A compound having the following formula:

13. The method according to claim 1, wherein R1, R2, R3, R4 and R8 are independently chosen from the group consisting of H and $(C_1\text{-}C_4)$alkyl.

* * * * *